United States Patent [19]

Klar

[11] Patent Number: 5,374,745

[45] Date of Patent: Dec. 20, 1994

[54] PROCESS FOR THE SYNTHESIS OF PROPARGYL ALCOHOLS AND THEIR USE FOR PRODUCTION OF PROSTAGLANDIN PRECURSORS

[75] Inventor: Ulrich Klar, Berlin, Germany

[73] Assignee: Schering Aktiengesellschaft, Berlin and Bergkamen, Germany

[21] Appl. No.: 930,506

[22] PCT Filed: Mar. 27, 1991

[86] PCT No.: PCT/EP91/00579

§ 371 Date: Sep. 29, 1992

§ 102(e) Date: Sep. 29, 1992

[30] Foreign Application Priority Data

Mar. 29, 1990 [DE] Germany ............... 4010339

[51] Int. Cl.$^5$ ............................ C07D 307/93
[52] U.S. Cl. ........................... 549/305; 549/311; 549/312
[58] Field of Search ............ 549/305, 311, 312

[56] References Cited

FOREIGN PATENT DOCUMENTS 284547 3/1988 European Pat. Off. .
2627422 6/1976 Germany .

OTHER PUBLICATIONS

T. Torisawa et al., "Efficient Inversion of Secondary Alcohols Using Cesium Acetate and 18-Crown-6", Chemistry Letters, pp. 1555–1556, 1984.
E. Dehmlow et al. "Darstellung von Alkinen aus Alkylhalogeniden mit festem Kalium-tert-butylat und Kronenether" Liebigs Annalen der Chemie, vol. 1–174, No. 1, Jan. 1980, pp. 1-13.

*Primary Examiner*—C. Warren Ivy
*Assistant Examiner*—Ba K. Trinh
*Attorney, Agent, or Firm*—Millen, White, Zelano, & Branigan

[57] ABSTRACT

The invention relates to a process for the production of prostaglandin precursors of formula I

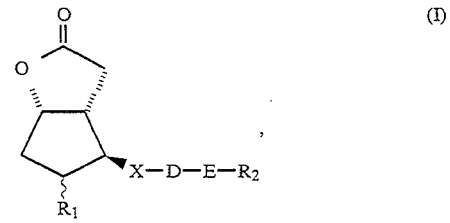

as well as their enantiomers in which
X is A—W or W—A,
A is a —C≡C— group,
W is a hydroxymethylene group, in which the OH group can be functionally modified by etherification or esterification,
D is a straight-chain or branched-chain alkylene group with 2–5 C atoms each or a

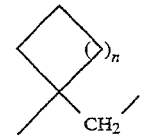

group,
n is 1 to 3,
E is a —C≡C— group or a —CR$_3$=CR$_4$ group with R$_3$ and R$_4$ each meaning a hydrogen atom or a C$_1$–C$_4$ alkyl group,
R$_1$ is a hydrogen atom or a hydroxy group, which can be functionally modified as in W,
R$_2$ is a straight-chain or branched-chain alkyl group with 1–7 C atoms, characterized in that vinyl bromides of formula II

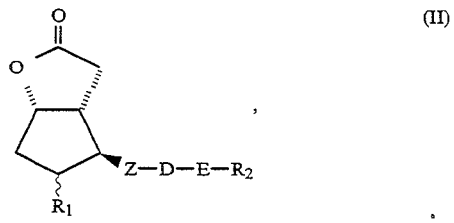

in which Z means the group (Abstract continued on next page.)

Abstract—continued

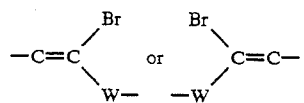

and $R_1$, W, D, E and $R_2$ have the above-indicated meanings and hydroxy groups unprotected in $R_1$ and W or represented by an optionally substituted benzoyl radical, a $C_1$-$C_6$ alkanoyl group, a tetrahydropyranyl radical, a tetrahydrofuranyl radical, a trialkylsilyl group or a diphenylalkylsilyl group each with alkyl meaning a $C_1$-$C_4$ alkyl, are reacted with anhydrous cesium acetate in the presence of 18-crown 6.

8 Claims, No Drawings

PROCESS FOR THE SYNTHESIS OF PROPARGYL ALCOHOLS AND THEIR USE FOR PRODUCTION OF PROSTAGLANDIN PRECURSORS

In the synthesis of prostaglandin analogs with a triple bond in position 13.14 (prostane numbering system), as they are described, for example, in EP 0284547, DE 3610556, DE 3725031, DE 3428266, DE 3427797, U.S. Pat. No. 4,628,110, the triple bond is introduced only in a relatively late synthesis stage with comparatively moderate yields. It has now surprisingly been found that starting from compounds of general formula II, the triple bond can be generated in very good yields under mild conditions by elimination of hydrobromic acid with anhydrous cesium acetate and 18-crown 6 already in an early synthesis stage.

The new process thus represents a valuable enrichment synthetic methodology.

The invention thus relates to a process for the production of prostaglandin precursors of formula I

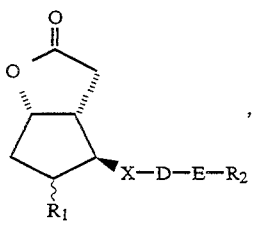

as well as their enantiomers in which
X is A—W or W—A,
A is a —C≡C— group,
W a hydroxymethylene group, in which the OH group can be functionally modified by etherification or esterification,
D is a straight-chain or branched-chain alkylene group with 2–5 C atoms each or a

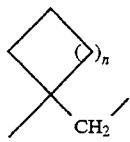

group,
n is 1 to 3,
E is a —C≡C— group or a —CR$_3$=CR$_4$ group with R$_3$ and R$_4$ each meaning a hydrogen atom or a C$_1$-C$_4$ alkyl group,
R$_1$ is a hydrogen atom or a hydroxy group, which can be functionally modified as in W,
R$_2$ is a straight-chain or branched-chain alkyl group with 1–7 C atoms, which is characterized in that vinyl bromides of formula II

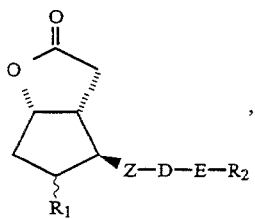

in which Z means the group

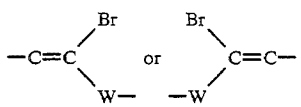

and R$_1$, W, D, E and R$_2$ have the above-indicated meanings and hydroxy groups unprotected in R$_1$ and W or represented by an optionally substituted benzoyl radical, a C$_1$-C$_6$ alkanoyl group, a tetrahydropyranyl radical, a tetrahydrofuranyl radical, a trialkylsilyl group or a diphenylalkylsilyl group each with alkyl meaning a C$_1$-C$_4$ alkyl, are reacted with anhydrous cesium acetate in the presence of 18-crown 6.

Examples

EXAMPLE 1

(1S,5R,6S,7R)-7-Hydroxy-6-[(3S,4S)-3-hydroxy-4-methyl-nona-1,6-diinyl]-2-oxabicyclo[3.3.0]octan-3-one:

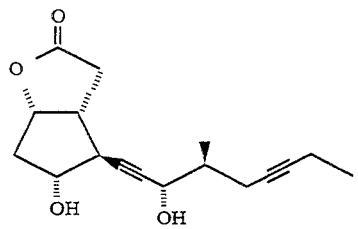

500 mg (1.35 mmol) of (1S,5R,6S,7R)-7-hydroxy-6-[(E)-(3S,4S)-2-bromo-3-hydroxy-4-methyl-1-nonen-6-inyl]-2-oxabicyclo[3.3.0]octan-3-one (for preparation see EP0284547) is dissolved in 40 ml of anhydrous toluene, mixed with 840 mg of anhydrous cesium acetate, 1.0 g of 18-crown 6 and the colorless, heterogeneous mixture is refluxed for 9 hours under an atmosphere of dry argon. After the cooling, it is concentrated by evaporation to about 20 ml and the mixture is purified by chromatography on about 100 ml of fine silica gel with ethyl acetate under pressure. 386 mg (1.33 mmol, 98%) of the title compound is isolated as colorless oil.

IR (Film): 3700–3100, 2970, 2920, 2230, 1755, 1450, 1415, 1370, 1320, 1200, 1085, 1025, 980 and 900 cm$^{-1}$.

EXAMPLE 2

(1S,5R,6S,7R)-7-Benzoyloxy-6-[(3R,4S)-3-hydroxy-4-methyl-nona-1,6-diinyl]-2-oxabicyclo[3.3.0]octan-3-one:

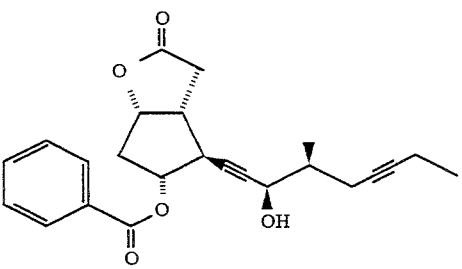

1.56 g (3.30 mmol) of (1S,5R,6S,7R)-7-benzoyloxy-6-[(E)-(3R,4S)-2-bromo-3-hydroxy-4-methyl-1-nonen-6-inyl]-2-oxabicylo[3.3.0]octan-3-one (for preparation see EP0284547) is reacted analogously to example 1 and after chromatographic purification, 1.15 g (2.73 mmol, 83%) of the title compound is isolated as colorless oil.

IR (Film): 3700–3100, 3060, 2970, 2920, 2870, 2230, 1770, 1715, 1600, 1450, 1365, 1315, 1270, 1180, 1110, 1070, 1030, 980, 900, 735 and 710 cm$^{-1}$.

EXAMPLE 5g (1S,5R,6R,7R)-6-[(E)-(3S,4S)-2-Bromo-3-hydroxy-4-methyl-non-1-en-6-inyl]-7-hydroxy-2-oxa-bicyclo[3.3.0]octan-3-one 3.12 g of (1S,5R,6R,7R)-6-[(E)-(3S,4S)-2-bromo-3-hydroxy-4-methyl-non-1-en-6-inyl]-7-benzoyloxy-2-oxa-bicyclo[3.3.0]octan-3-one was dissolved in 18 ml of reagent-grade methanol, mixed with 290 mg of finely powdered potassium carbonate and allowed to stir for 3 hours at 25° C. By adding a 50% hydrochloric acid, it was adjusted to pH 7 and concentrated by evaporation at 30° C. in a water jet vacuum. The residue was taken up in methylene chloride, filtered on magnesium sulfate and Celite, again concentrated by evaporation in a water jet vacuum and chromatographed under pressure on about 200 ml of fine silica gel by using a gradient of hexane/ethyl acetate. 2.00 g (82%) of the title compound was isolated as colorless oil.

IR (film): 3400, 2950, 2910, 1755, 1640, 1440, 1415, 1340, 1300, 1180, 1075, 1030, 968, 905 cm $^{-1}$.

EXAMPLE 5h
(1S,5R,6R,7R)-6-[(E)-(3S,4S)-2-Bromo-3-hydroxy-4-methyl-non-1-en-6-inyl]-7-benzoyloxy-2-oxa-bicyclo[3.3.0]octan-3-one 16.7 g of (1S,5R,6R,7R)-6-[(E)-(4S)-2-brom-3-oxo-4-methyl-non-1-en-6-inyl]-7-benzoyloxy-2-oxa-bicyclo[3.3.0]octan-3-one was reduced analogously to example 2g. After chromatographic purification, 4.1 g (24%) of the title compound as well as 6.6 g of (1S,5R,6R,7R)-6-[(E)-(3S,4S)-2-brom-3-oxo-4-methyl-non-1-en-6-inyl]-7-benzoyloxy-2-oxa-bicyclo[3.3.0]octan-3-one (39%) were isolated.

IR (film): 3460 (broad), 3060, 2970, 2930, 1770, 1714, 1602, 1450, 1317, 1272, 1178, 1115, 1070, 1026, 737, 715 cm$^{-1}$.

EXAMPLE 5i
(1S,5R,6R,7R)-6-[(E)-(4S)-2-Brom-3-oxo-4-methyl-non-1-en-6-inyl]-7-benzoyloxy-2-oxa-bicyclo[3.3.0]octan-3-one The solution of 13.7 g of dimethyl-[(3S)-2-oxo-3-methyl-oct-5-inyl] phosphonate in 135 ml of dimethoxyethane at 0° C. was instilled with exclusion of moisture in a suspension of 2.58 g of NaH in 225 ml of dimethoxyethane. After 20 minutes of stirring, the now clear solution was mixed with 9.89 g of finely powdered N-bromosuccinimide, stirred for 1 more hour at 0° C., the solution of 12.3 g of Corey lactone was instilled and allowed to react for another 2 hours at 0° C. With vigorous stirring in 800 ml, a 10% aqueous ammonium chloride solution was infused, extracted several times with a total of 1.5 l of diethyl ether, the organic phase was rewashed with water, dried on magnesium sulfate and after filtration and concentration by evaporation in a vacuum, 27.4 g of a yellow crude oil was isolated, which was chromatographically purified under pressure by a gradient of hexane and ethyl acetate. 16.9 g (72%) of the title compound was isolated as colorless oil.

IR (film): 2970, 2920, 1765, 1720, 1600, 1450, 1360, 1315, 1270, 1170, 1105, 1070, 965 cm$^{-1}$.

EXAMPLE 2g (1S,5R,6R,7R)-6-[(E)-(3S,4RS)-3-Hydroxy-4-methyl-oct-1-en-6-inyl]-7-benzoyloxy-2-oxabicyclo-[3.3.0]octan-3-one The solution of 12.5 g of (1S,5R,6R,7R)-6-[(E)-(4RS)-3-oxo-4-methyl-oct-1-en-6-inyl]-7-benzoyloxy-2-oxabicyclo[3.3.0 octan3-one in a mixture of 300 ml of methanol and 80 ml of tetrahydrofuran was mixed with exclusion of moisture at −40° C. with 1.84 g of CeCl$_3$.7-H$_2$O and then in portions with a total of 1.85 g of sodium borohydride. After 1 hour at −40° C., it was mixed with 50 ml of acetone and 10 ml of a 2n H$_2$SO$_4$ and adjusted with 10% aqueous citric acid to pH 7. It was allowed to heat to room temperature, concentrated by evaporation in a vacuum to a residual volume of 100 ml, mixed with water and extracted several times with a total of 800 ml of dichloromethane. The combined organic extracts were washed with water, dried on magnesium sulfate and concentrated by evaporation in a vacuum. 13.6 g of a yellow oil, which was chromatographed under pressure on silica gel with ether/pentane, was obtained. In addition to small amounts of initial material, 7.43 g (59%) of the title compound and as more polar components, 5.12 g (41%) of (1S,5R,6R,7R)-6-[(E)-(3R,4RS) -3 -hydroxy-4-methyl-oct-1-en-6-inyl)]-7-benzoyloxy-2-oxabicyclo-[3.3.0]octan-3 -one were isolated.

IR (film): 3460, 2970, 2930, 1760, 1720, 1455, 1320, 1270, 1175, 1110, 1070, 740, 715 cm$^{-1}$.

EXAMPLE 3

(1S, 5R,6S,7R) -7-Benzoyloxy-6-[(3S,4S)-3-(4-nitrobenzoyloxy)-4-methyl-nona-1,6-diinyl]-2-oxa-bicyclo[3.3.0]octan-3-one:

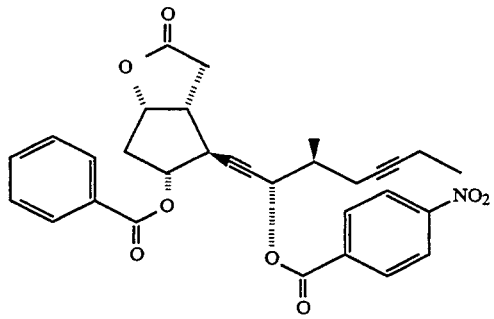

280 mg of (1S,5R,6S,7R)-7-Benzoyloxy-6-[(E)-(3S,4S)-2-bromo-3-(4-nitrobenzoyloxy)-4-methyl-1-nonen-6-inyl]-2-oxabicyclo[3.3.0]octan-3-one as crystalline adduct is reacted with 1.4 equivalents of 1,2-bis-ethoxy-carbonylhydrazine (corresponds to 321 μmol) analogously to example 1 and after chromatographic purification, 91 mg (167 μmol, 52%) of the title compound is isolated as solid in addition to 24% initial material.

IR (KBr): 3110, 3070, 2970, 2930, 2870, 2240, 1770, 1720, 1605, 1525, 1450, 1345, 1315, 1265, 1175, 1110, 1070, 965, 870, 850 and 710 cm$^{-1}$.

EXAMPLE 4

(1S,5R,6R,7R)-7-Benzoyloxy-6-[(1R,4S or 1S,4S)-1-hydroxy-4-methyl-nona-2,6-diinyl]-2-oxabicyclo[3.3.0]octan-3-one:

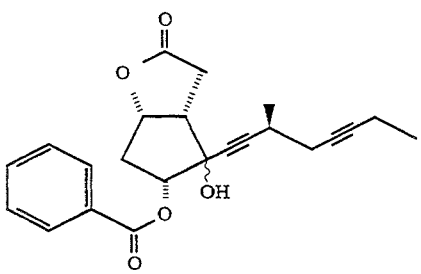

150 mg (315 μmol) of (1S,5R,6R, 7R)-7-benzoyloxy-6-[(Z)-(1R,4S or 1S,4S) -1-hydroxy-2-bromo-4-methyl-non-2-en-6-inyl]-2-oxabicyclo[3.0.0]octan-3-one (polar alcohol of example 4a) is reacted analogously to example 1 and after chromatographic purification, 81 mg (203 μmol, 65%) of the title compound is isolated as colorless oil.

IR (Film): 3600–3100, 3060, 2970, 2965, 2935, 2230, 1770, 1710, 1600, 1450, 1375, 1315, 1270, 1175, 1110, 1070, 1045, 1025 and 710 cm$^{-1}$.

EXAMPLE 4a (1S,5R,6R,7R)-7-Benzoyloxy-6-[(Z)-(1R,4S)-1-hydroxy-2-bromo-4-methyl-non-2-en-6-inyl]-2-oxabicyclo[3.3.0]octan-3-one and (1S,5R,6R,7R)-7-benzoyloxy-6-[(Z)-(1S,4S)-1-hydroxy-2-bromo-4-methyl-non-2-en-6-inyl]-2-oxabicyclo[3.3.0]octan-3-one:

17.6 g (37.1mmol) of (1S,5R,6S,7R)-7-benzoyloxy-6-[(E)-(3R,4S)-2 -bromo-3-hydroxy-4-methyl-1-nonen-6-inyl]-2-oxabicyclo[3.3.0]octan-3-one (for preparation see EP0284547) is dissolved in 260 ml of acetone, cooled under an atmosphere of dry argon to −30° C. and 20 ml of a standardized Jones solution is instilled within 10 minutes. It is stirred for another 1.5 hours at −20° C., excess oxidizing agent is decomposed by adding 25 ml of isopropanol, allowed to heat to 20° C., mixed with 300 ml of water and extracted several times with a total of 600 ml of diethyl ether. The combined organic extracts are washed with water and saturated sodium chloride solution until neutral reaction, dried on magnesium sulfate and the residue obtained after filtration and removal of the solvent is purified by chromatography on about 800 ml of fine silica gel by using an n-hexane/ethyl acetate mixture. In addition to 11.3 g (23.9 mmol, 64%) of (1S,5R,6S,7R)-7-benzoyloxy-6-[(E)-(4S)-2-brom-3-oxo-4-methyl-1-nonen-6-inyl]-2-oxa-bicyclo[3.3.0]octan-3-one, 3.59 g (7.58 mmol, 26%) of (1S,5R,6R,7R)-7-benzoyloxy-6-[(Z)-(4S)-1-oxo-2-bromo-4-methyl-non-2-en-6-inyl]-2-oxabicyclo[3.3.-0]octan-3-one is isolated. The latter compound is dissolved in 45 ml of anhydrous methanol, cooled under an atmosphere of dry argon to −45° C., mixed in portions with a total of 520 mg of sodium borohydride and stirred for 30 more minutes at −45° C. Excess reducing agent is decomposed by adding 0.8 ml of acetone, allowed to heat to 20° C., mixed with water and extracted several times with diethyl ether. The combined organic extracts are washed with water and saturated sodium chloride solution until neutral reaction, dried magnesium sulfate and the residue obtained after filtration and removal of the solvent is purified by chromatography on about 200 ml of fine silica gel by using a dichloromethane/ethyl ether mixture. 1.79 g (3.76 mmol, 50%) of the nonpolar alcohol as well as 528 mg (1.11 mmol, 15%) of the polar alcohol are isolated.

What is claimed is:

1. Process for the production of prostaglandin precursors of formula I

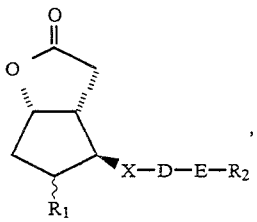

as well as their enantiomers in which
X is A—W or W—A,
A is a —C≡C— group,
W is a hydroxymethylene group, in which the OH group can be functionally modified by etherification or esterification,
D is a straight-chain or branched-chain alkylene group with

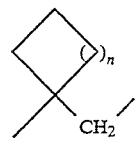

group,
n is 1 to 3,
E is a —C≡C— group or a —CR$_3$=CR$_4$ group with R$_3$ and R$_4$ each meaning a hydrogen atom or a C$_1$-C$_4$ alkyl group,
R$_1$ is a hydrogen atom or a hydroxy group, which can be functionally modified as in W,
R$_2$ is a straight-chain or branched-chain alkyl group with 1-7 C atoms, characterized in that vinyl bromides of formula II

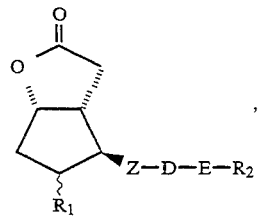

in which Z means the group

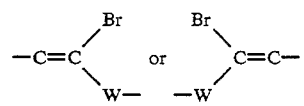

and R$_1$, W, D, E and R$_2$ have the above-indicated meanings and hydroxy groups unprotected in R$_1$ and W or represented by an optionally substituted benzoyl radical, a C$_1$-C$_6$ alkanoyl group, a tetrahydropyranyl radical, a tetrahydrofuranyl radical, a trialkylsilyl group or a diphenylalkylsilyl group each with alkyl meaning a C$_1$-C$_4$ alkyl, are reacted with anhydrous cesium acetate in the presence of 18-crown 6.

2. A process according to claim 1, wherein the prostaglandin precursor of formula I is a) (1S,5R,6S,7R)-7-Hydroxy-6-[(3S,4S)-3-hydroxy-4-methyl-nona-1,6-diinyl]-2-oxabicyclo[3.3.0]octan-3-one; or b) (1S,5R,6S,7R)-7-Benzoyloxy-6-[(3R,4S)-3-hydroxy-4-methyl-nona-1,6-diinyl]-2-oxabicyclo[3.3.0]octan-3-one;

c) (1S,5R,6S,7R)-7-Benzoyloxy-6-[(3S,4S)-3-(4-nitrobenzoyloxy)-4-methyl-nona-1,6-diinyl]-2-oxabicyclo[3.3.0]octan-3-one;

d) (1S,5R,6R,7R)-7-Benzoyloxy-6-[(1R,4S or 1S,4S)-1-hydroxy-4-methyl-nona-2,6-diinyl]-2-oxabicyclo[3.3.0]octan-3-one;

e) (1S,5R,6R,7R)-7-Benzoyloxy-6-[(Z)-(1R,4S)-1-hydroxy-2-bromo-4-methyl-non-2-en-6-inyl]-2-oxa-bicyclo[3.3.0]octan-3-one; or f) (1S,5R,6R,7R)-7-Benzoyloxy-6-[(Z)-(1S,4S)-1-hydroxy-2-bromo-4-methyl-non-2-en-6-inyl]-2-oxabicyclo[3.3.0]octan-3-one.

3. A process according to claim 1, wherein $R_1$ is OH.

4. A process according to claim 1, wherein $R_1$ is benzyloxy.

5. A process according to claim 1, wherein X is A—W; and W is a hydroxymethylene group.

6. A process according to claim 1, wherein X is A—W; and W is a hydroxymethylene group, in which the OH is functionally modified by a 4-nitrobenzoyloxy group.

7. A process according to claim 1, wherein X is A—W; and W is a hydroxymethylene group.

8. A process according to claim 1, wherein X is A—W; E is —C≡C—; and $R_2$ is —CH$_2$CH$_3$.

* * * * *

UNITED STATES PATENT AND TRADEMARK OFFICE
CERTIFICATE OF CORRECTION

PATENT NO. : 5,374,745
DATED : December 20, 1994
INVENTOR(S) : Ulrich KLAR

It is certified that error appears in the above-indentified patent and that said Letters Patent is hereby corrected as shown below:

Claim 1; column 6, line 21:  After "with" insert
-- 2-5 C atoms each or a --.

Signed and Sealed this

Fourth Day of April, 1995

Attest:

BRUCE LEHMAN

Attesting Officer                Commissioner of Patents and Trademarks